United States Patent [19]
Noguchi et al.

[11] Patent Number: 5,277,543
[45] Date of Patent: Jan. 11, 1994

[54] DEVICE FOR MONITORING ABRASION LOSS OF A THRUST BEARING IN A SUBMERGED MOTOR PUMP

[75] Inventors: Shotaro Noguchi; Shikou Kiyota, both of Fukui; Michio Nakagawa; Akira Yasue, both of Kanagawa; Akio Uehara, Chiba, all of Japan

[73] Assignees: Doryokuro Kakunenryo Kathatsu Jigyodan; Fuji Electric Co., Ltd.; Sumitomo Heavy Industries, Ltd., all of Japan

[21] Appl. No.: 919,946

[22] Filed: Jul. 27, 1992

[30] Foreign Application Priority Data

Aug. 8, 1991 [JP] Japan .................. 3-199330

[51] Int. Cl.$^5$ .............. F04D 27/00; G01M 13/04
[52] U.S. Cl. .................. 415/118; 384/448; 73/593; 367/99
[58] Field of Search .......... 415/118, 180; 417/366, 417/369, 423.8; 384/448; 73/593, 168; 367/99

[56] References Cited

U.S. PATENT DOCUMENTS

| | | | |
|---|---|---|---|
| 3,572,976 | 3/1971 | Sato | 417/369 |
| 3,999,897 | 12/1976 | Strub | 417/366 X |
| 4,198,191 | 4/1980 | Pierce | 417/369 |
| 4,302,963 | 12/1981 | Collins | 415/118 X |
| 4,543,649 | 9/1985 | Head et al. | 367/99 X |
| 4,825,423 | 4/1989 | Yamanaka | 367/99 |
| 4,995,259 | 2/1991 | Khuri-Yakub et al. | 73/593 |
| 5,056,368 | 10/1991 | Kawasaki et al. | 73/593 X |

Primary Examiner—Edward K. Look
Assistant Examiner—Michael S. Lee
Attorney, Agent, or Firm—Lorusso & Loud

[57] ABSTRACT

A submerged motor pump is provided in a piping system or connected to a pressure vessel, and a pump and a motor are immersed in the fluid. A rotor rotatable together with a pump impeller is fixed to a rotor shaft. The rotor shaft is supported by a thrust bearing. A cover is provided facing the end of the rotor shaft and carries an ultrasonic sensor on its outside surface. The ultrasonic sensor projects ultrasonic wave toward the end of the rotor shaft and detects the echo therefrom so as to measure the distance between the end of the rotor shaft and the inside surface of the cover, i.e. the surface thereof in contact with the fluid. The inside surface of the cover includes a concave spherical surface which faces the end of the rotor shaft and substantially converges the main beam of the ultrasonic wave to the end of the rotor shaft, preventing reduction of sound pressure of the ultrasonic wave.

15 Claims, 5 Drawing Sheets

DEVICE FOR MONITORING ABRASION LOSS OF A THRUST BEARING IN A SUBMERGED MOTOR PUMP

BACKGROUND OF THE INVENTION

1. FIELD OF THE INVENTION

The present invention relates to a device for monitoring abrasion loss of a thrust bearing in a submerged motor pump.

2. DESCRIPTION OF THE RELATED ART

A plant which handles a fluid of a special kind or a fluid at high temperature and high pressure, such as a thermal electric power plant, a nuclear power plant, an oil (refining) plant or a chemical plant, normally employs an enclosed submerged motor pump comprising a pump and motor, such as a canned motor or a wet stator motor, which are formed together without a shaft seal between the pump and the motor.

If a detector is provided inside the motor for examining the motor, the construction of the submerged motor pump becomes complicated. Moreover, if a part of the detector should come off or break up, the separated part or portion will very likely hit and damage a bearing, a stator or a rotor of the motor and cause trouble.

Therefore, an ammeter, a thermometer and a vibrometer for examining the motor indirectly are mounted on the outside of the motor casing in a known submerged motor pump.

However, since the motor is indirectly examined by observing the values indicated by the ammeter, the thermometer and the vibrometer or the transition of the indicated values, it is extremely difficult to precisely quantitate abrasion loss of a thrust bearing in an early stage. The abrasion loss of the thrust bearing is one of the important factors to be monitored in a submerged motor pump.

In the submerged motor pump, a pump shaft connected to a pump impeller is radially supported by a journal bearing and axially supported by the thrust bearing. Abrasion loss of the journal bearing is comparatively easy to detect because such abrasion loss is likely to cause a change in the vibration. On the other hand, abrasion loss of the thrust bearing is difficult to detect because it hardly causes any significant change in the values indicated by the ammeter, the thermometer and the vibrometer or the transition of these values. Therefore, it is not detected before the abrasion loss of the thrust bearing has reached an abnormal level. Abrasion loss of the thrust bearing can be accurately measured only when the submerged motor pump is disassembled.

In practice, therefore, a submerged motor pump is periodically disassembled to check out abrasion loss of the thrust bearing and replace worn parts if necessary. The interval between such periodical inspection is determined based on experience.

However, the rate of abrasion of the thrust bearing greatly varies depending on operating hours, times of starting and stopping, and contaminants (solid materials) in the fluid. In some cases, abrasion of the thrust bearing progresses much faster than expected.

SUMMARY OF THE INVENTION

The present invention is intended to solve the above problems of the conventional submerged motor pump. It is an object of the present invention to provide a device for monitoring abrasion loss of a thrust bearing in a submerged motor pump, which accurately quantitates abrasion loss of the thrust bearing by detection from outside a pump and a motor casing continuously or at desired occasions during the operation of the pump. Thus, the submerged motor pump does not need to be disassembled for detection of abrasion loss of the thrust bearing. Such a monitoring device will help improve reliability of the submerged motor pump and precision in predicting occurrence of an abnormality or estimating residual life.

In general, a submerged motor pump is placed in the piping system or connected to a pressure vessel, and the pump and the motor are immersed in a fluid together.

A rotor is connected and rotated together with a pump impeller in the pump. The rotor is fixed to a rotor shaft and supported by a thrust bearing. Thus, thrust load is imposed on the thrust bearing.

According to the present invention, a cover is arranged so as to face the end of the rotor shaft. An ultrasonic sensor is provided on the outside surface of the cover. The ultrasonic sensor projects ultrasonic waves into the end of the rotor shaft and receives echo therefrom in order to detect the distance between the end of the rotor shaft and an inner peripheral surface of the cover that is in contact with a fluid (referred to as the "fluid contact surface" hereinafter).

The fluid contact surface of the cover is flat and smooth, in general. However, e.g., where the area of the end of the rotor shaft is small, the fluid contact surface may be formed as a concave spherical surface so as to focus ultrasonic waves on the end of the rotor shaft. Detection precision of the ultrasonic sensor is thus improved. Such a concave spherical form of the fluid contact surface will reduce diffusion of the main beam of ultrasonic waves and substantially prevent reduction of sound pressure of the ultrasonic waves which reaches the end of the rotor shaft. In addition, a cap nut may be used to cover the end of the rotor shaft.

The actual distance between the fluid contact surface of the cover and the end of the rotor shaft is calculated using the measurements of the ultrasonic sensor.

A temperature sensor and a pressure sensor are provided which detect the temperature and the pressure of the fluid between the fluid contact surface and the end of the rotor shaft. A calculator uses a temperature detected by the temperature sensor and a pressure detected by the pressure sensor to calculate the sound velocity in the fluid. The actual distance between the fluid contact surface of the cover and the end of the rotor shaft is calculated from a sound velocity in the fluid provided by the calculator, a sound velocity in the fluid obtained beforehand when the measuring instruments are calibrated in the mockup test, and a measurement provided by the ultrasonic sensor.

A displacement of the rotor shaft, i.e., an abrasion loss of the thrust bearing, is obtained from a change in the actual distance between the fluid contact surface of the cover and the end of the rotor shaft, which change occurs as time progresses during operation.

The construction and features of the present invention of a device for monitoring abrasion loss of a thrust bearing in a submerged motor pump will become apparent from the following description of the preferred embodiments with reference to the attached drawings.

DESCRIPTION OF PREFERRED EMBODIMENT

Embodiments of the present invention will be described hereinafter with reference to the drawings.

Figure 1:
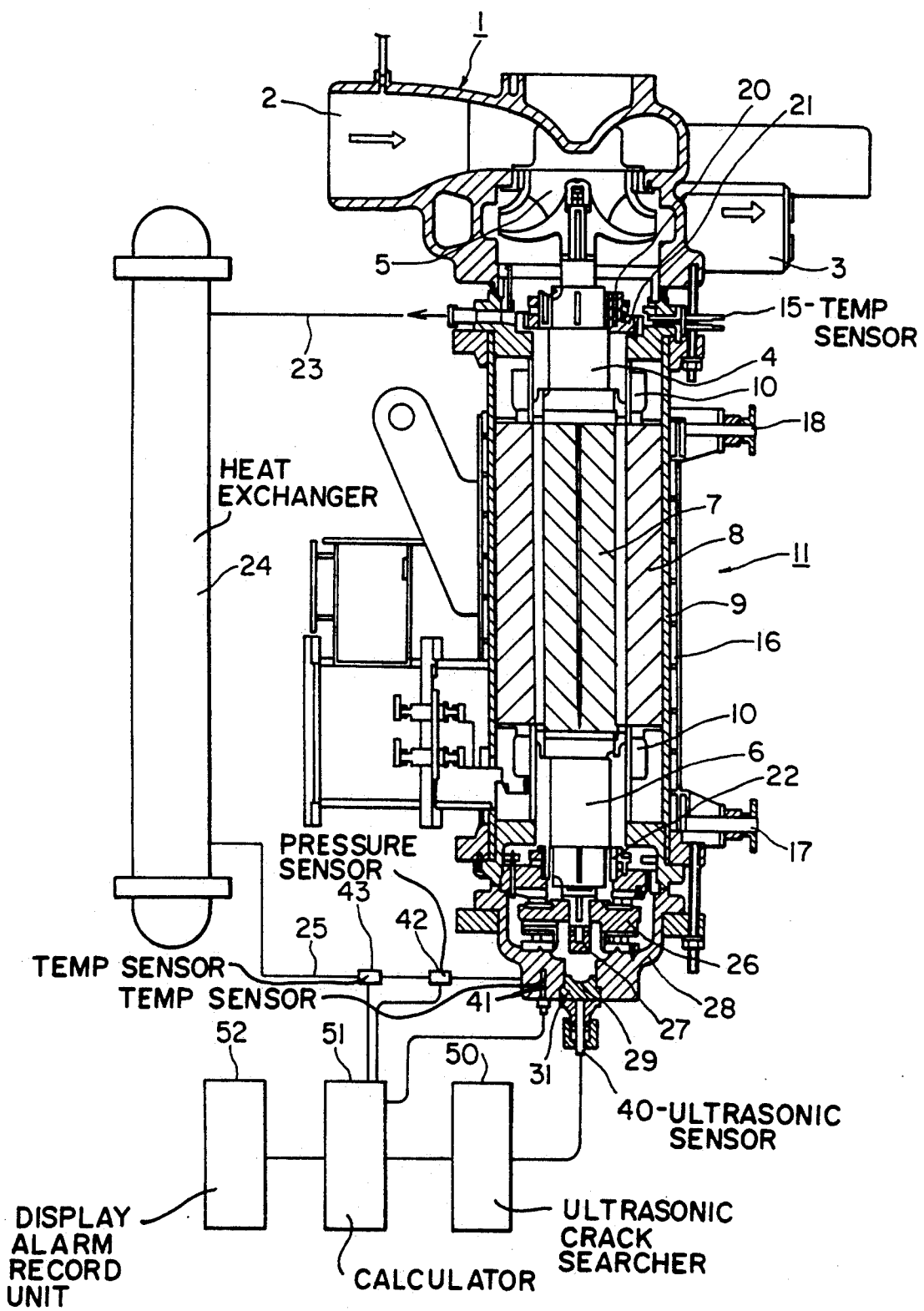
FIG. 1 is a schematic view of a device for monitoring abrasion loss of a thrust bearing in a submerged motor pump, according to the first embodiment of the present invention.

FIG. 1 shows a pump case 1, a fluid inlet 2, a fluid outlet 3, a pump shaft 4, and a pump impeller 5 which is rotated by the pump shaft 4. The pump shaft 4 is connected to a rotor shaft 6, to which a rotor 7 is fixed. A stator 8 is provided around the rotor 7. A stator frame 9 supports the stator 8. A stator coil 10 is provided around the stator 8. Thus, when the stator coil 10 is supplied with driving current, the rotor 7 rotates. The rotor 7, the stator 8 and the stator coil 10 constitute a motor 11.

A temperature sensor supporter 15 supports a temperature sensor which detects the temperature of the fluid. A water jacket 16 is formed around the stator frame 9 and constitutes a motor casing. A stator coolant inlet 17 is connected to a bottom portion of the water jacket 16. The stator coolant is fed through the stator coolant inlet 17 into the water jacket 16, cools the stator 8 as it goes up through the water jacket 16, and then is let out through a stator coolant outlet 18.

The pump shaft 4 is rotatably supported by an upper journal bearing 20, which is supported by an upper bearing housing 21. The rotor shaft 6 is rotatably supported by a lower journal bearing 22 and is rotated together with the pump shaft 4.

Space inside the stator 8 is connected to space inside the pump case 1. The fluid let in through the fluid inlet 2 is sent to the fluid outlet 3 by rotation of the pump impeller 5. A fluid offtake passage 23, a heat exchanger 24 and a fluid return passage 25 are provided. The fluid inside the stator 8 is extracted through the fluid offtake passage 23 and then sent to the heat exchanger 24. After the fluid is cooled by heat exchange between the fluid and coolant in the heat exchanger 24, the fluid is sent through the fluid return passage 25 to the submerged motor pump to cool the motor 11.

The end of the rotor shaft 6 is rotatably supported by a thrust bearing 26. Thus, thrust load from the rotor shaft is imposed on the thrust bearing 26.

Figure 2:
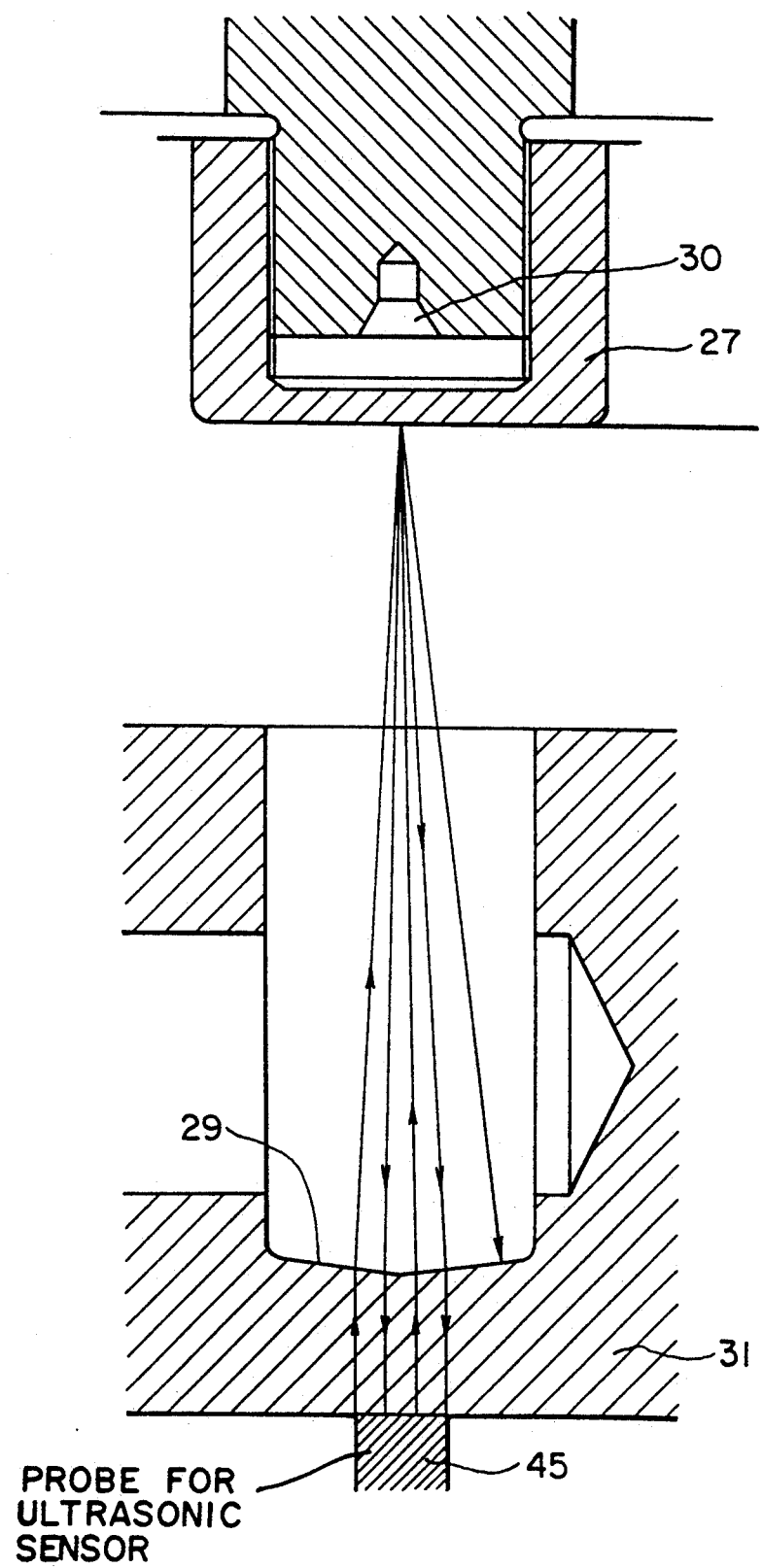
FIG. 2 illustrates ultrasonic waves in association with a concave spherical surface.
Figure 3:
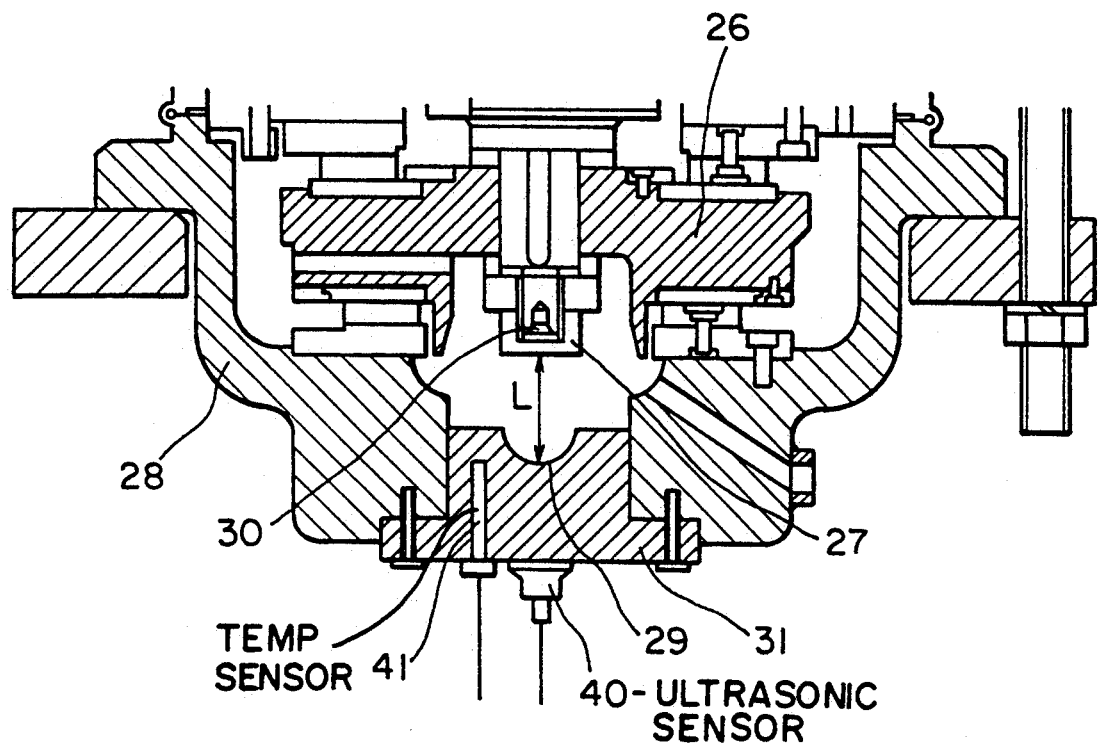
FIG. 3 is an enlarged view of essential portions of the monitor device for monitoring abrasion loss of a thrust bearing in a submerged motor pump according to the first embodiment of the present invention.

Referring to FIGS. 1, 2 and 3, a shaft-end cap nut 27 is provided for covering the end surface of the rotor shaft 6 if the end surface of the rotor shaft 6 is not flat. An end cover 28 is fixed to the bottom end of the water jacket 16 by bolts and nuts so as to enclose the thrust bearing 26. The figure further shows: a concave spherical surface 29; a shaft-end center hole 30 formed in the end surface of the rotor shaft 6 and used for machining; a sensor-mounting cover 31 detachably mounted in the end cover 28 and having the concave spherical surface 29 on its fluid contact surface.

An ultrasonic sensor 40 is a non-contact type distance detector and detects the distance between the concave spherical surface 29 and the end of the rotor shaft 6. The end of the rotor shaft 6 is the end surface of the rotor shaft 6 if the shaft-end cap nut 27 is not provided, and is the end surface of the shaft-end cap nut 27 if the shaft-end cap nut 27 is provided. Instead of the ultrasonic sensor 40, a non-contact type distance detector may use electromagnetic waves or sound waves other than ultrasonic waves.

A temperature sensor 41 detects the temperature of the sensor-mounting cover 31. A pressure sensor 42 is provided in the fluid return passage 25 and detects the pressure of the fluid between the concave spherical surface 29 and the end surface of the shaft-end cap nut 27. Another temperature sensor 43 is provided in the fluid return passage 25 and detects the temperature of the fluid between the concave spherical surface 29 and the end surface of the shaft-end cap nut 27. The figures further show a probe 45 for the ultrasonic sensor 40, an ultrasonic crack searcher 50 (with a digital display of measured distance), a calculator 51 and a display-alarm-record unit 52.

According to the present invention, the ultrasonic sensor 40, provided on the outside surface of the sensor-mounting cover 31, at a position facing the end of the rotor shaft 6, projects ultrasonic wave toward the shaft-end cap nut 27 and detects the echo therefrom in order to measure the distance L between the concave spherical surface 29 and the end surface of the shaft-end cap nut 27.

The end surface of the rotor shaft 6 is a flat surface perpendicular to the axis of the shaft. As shown in FIG. 2, if the shaft-end center hole 30 for machine processing formed in the end surface of the rotor shaft 6 must be preserved, the end surface of the rotor shaft 6 is covered with the shaft-end cap nut 27 in order to provide a flat and smooth surface. The shaft-end cap nut 27 facilitates adjustment of the distance L (in FIG. 3) to the concave spherical surface 29 and focusing of ultrasonic wave.

As shown in FIG. 3, the outside surface of the sensor-mounting cover 31, on which surface the ultrasonic sensor 40 is mounted, is formed as a flat surface perpendicular to the axis of the rotor shaft 6. The fluid contact surface of the sensor-mounting cover 31 is formed as a concave spherical surface 29 so as to focus ultrasonic waves on the reflection surface, i.e., the end surface of the shaft-end cap nut 27. Thus, detection precision of the ultrasonic sensor 40 is improved. In detail, the concave spherical surface 29 substantially prevents diffusion of the main beam of the ultrasonic wave propagating therefrom into the fluid, and thus substantially prevents reduction of sound pressure of the ultrasonic wave reaching the end surface of the shaft-end cap nut 27. Therefore, sensitivity of the measurement system can be set low so that the measurement system will not be substantially affected by electric noise.

An opening is formed in the end cover 28 at a portion thereof facing the end of the rotor shaft 6. The sensor-mounting cover 31 is detachably fitted in the opening. The ultrasonic sensor 40 and the temperature sensor 41 are mounted on the sensor-mounting cover 31.

The temperature sensor 43 and the pressure sensor 42 detect the temperature and the pressure, respectively, of the fluid between the concave spherical surface 29 and the end surface of the shaft-end cap nut 27. Using the temperature and the pressure detected by the respective sensors 43 and 42, the calculator 51 calculates a sound velocity in the fluid. Then, the calculator 51 calculates the actual distance between the concave spherical surface 29 and the end surface of the shaft-end cap nut 27, using the sound velocity in the fluid provided by its own calculation, the sound velocity in the fluid obtained beforehand when the measuring instruments are calibrated in the mockup test, and the distance L provided by detection by the ultrasonic sensor 40.

A displacement of the rotor shaft 6, i.e., an abrasion loss of the thrust bearing 26, is obtained from a time-related change in the actual distance between the concave spherical surface 29 and the end surface of the shaft-end cap nut 27.

The ultrasonic sensor 40 and the temperature sensor 41 may be mounted directly on the end cover 28, without using the sensor-mounting cover 31.

Figure 4:
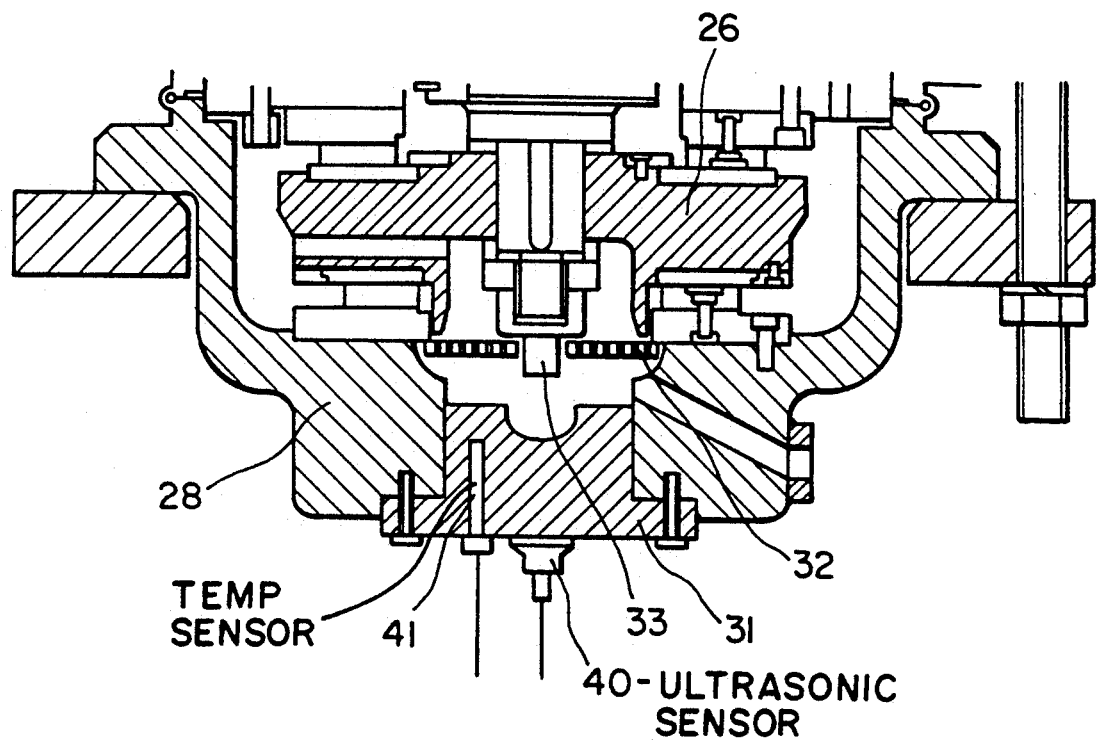
FIG. 4 is an enlarged view of essential portions of the monitor device for monitoring abrasion loss of a thrust bearing in a submerged motor pump according to the second embodiment of the present invention.

FIG. 4 is an enlarged view of essential portions of a device for monitoring the abrasion loss of a thrust bearing in a submerged motor pump, according to the second embodiment of the present invention. If a barrier, such as a strainer 32, is provided between the end surface of a rotor shaft (FIG. 1) and a sensor-mounting cover 31 as shown in FIG. 4, a cap nut 33 having a guide rod may be used to cover the end surface of the rotor shaft 6 so that the guide rod portion of the cap nut 33 extends through the strainer 32. Such construction will prevent the strainer 32 from scattering the main beam of the ultrasonic waves.

Figure 5:
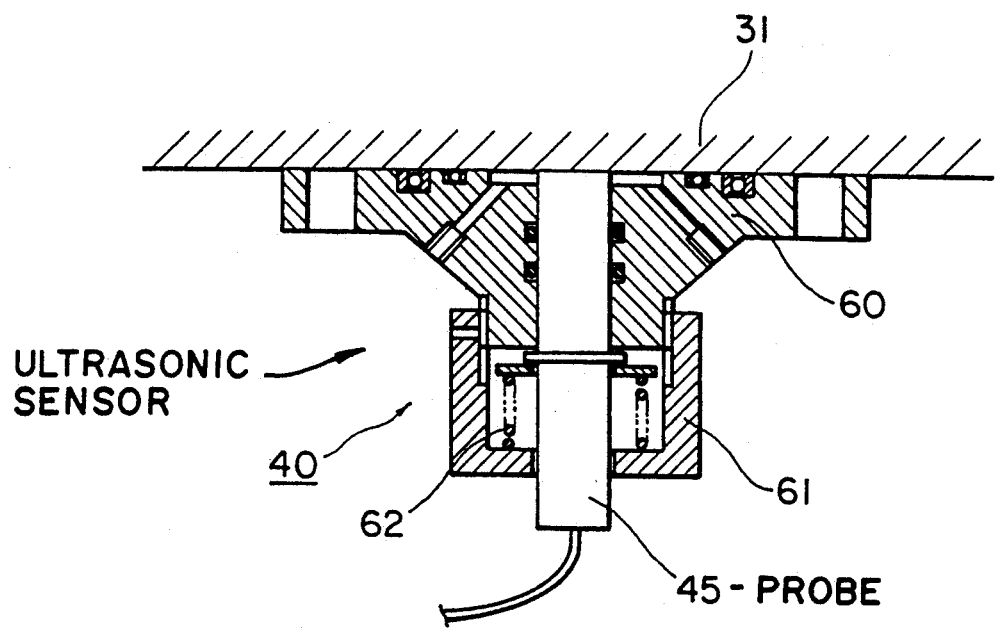
FIG. 5 illustrates mounting of an ultrasonic sensor in a monitor device for monitoring abrasion loss of a thrust bearing in a submerged motor pump according to the present invention.

FIG. 5 illustrates mounting of an ultrasonic sensor in a device for monitoring the abrasion loss of a thrust bearing in a submerged motor pump, according to the present invention. The figure shows a sensor holder 60 providing a predetermined contact pressure, a cap nut 61 and a spring 62. A gap on top of the sensor holder 60 is filled with grease or oil so that air is forced out from between the top end surface of the probe 45 of the ultrasonic sensor 40 and the outside surface of the sensor-mounting cover 31. The spring 62 and the cap nut 61 press the ultrasonic sensor 40 onto the outside surface of the sensor-mounting cover 31 with a predetermined contact pressure. Such a construction will contribute to stable propagation of ultrasonic waves between the probe 45 and the sensor-mounting cover 31 and substantially prevent errors in the distance detection.

As described above, the sensor-mounting cover 31 is provided facing the shaft-end cap nut 27, and the ultrasonic sensor 40 is provided on the outside surface of the sensor-mounting cover 31. The ultrasonic sensor 40 projects ultrasonic waves toward the end surface of the shaft-end cap nut 27 and detects the echo therefrom so as to obtain a distance L between the concave spherical surface 29 and the end surface of the shaft-end cap nut 27.

Since the ultrasonic sensor 40 is provided outside the motor 11, the construction of the submerged motor pump can be simplified.

The fluid contact surface, i.e., the surface facing the end surface of the shaft-end cap nut 27, of the sensor-mounting cover 31 is usually formed as a flat and smooth surface. However, for example, in a case where the area of the end surface of the shaft-end cap nut 27 is small, the fluid surface may be in a form like the concave spherical surface 29, in order to improve detection by the ultrasonic sensor 40. Such a concave spherical surface will reduce diffusion of the main beam of ultrasonic waves and substantially prevent reduction of sound pressure of the ultrasonic waves which reaches the end surface of the shaft-end cap nut 27. Therefore, sensitivity of the measurement system can be set low so that the measurement system will not be substantially affected by electric noise.

The actual distance between the concave spherical surface 29 and the end surface of the shaft-end cap nut 27 is calculated from the distance L detected by the ultrasonic sensor 40 by the calculating means described below.

In detail, the temperature sensor 43 and the pressure sensor 42 detect the temperature and the pressure, respectively, of the fluid between the concave spherical surface 29 and the end surface of the shaft-end cap nut 27. Using a temperature and a pressure detected by the respective sensors 43 and 42, the calculator 51 calculates a sound velocity in the fluid. Then, the calculator 51 calculates the actual distance between the concave spherical surface 29 and the end surface of the shaft-end cap nut 27, using the sound velocity in the fluid provided by its own calculation, the sound velocity in the fluid obtained beforehand when the measuring instruments are calibrated in the mockup test, and the distance L provided by detection of the ultrasonic sensor 40.

A displacement of the rotor shaft 6, i.e., an abrasion loss of the thrust bearing 26, is obtained from a time-related change in the actual distance between the concave spherical surface 29 and the end surface of the shaft-end cap nut 27.

While the present invention has been described with respect to what are presently considered to be the preferred embodiments, it is to be understood that the invention is not limited to the disclosed embodiments. On the contrary, the invention is intended to cover various modifications and equivalent arrangements included within the spirit and scope of the appended claims.

What we claim is:

1. In a submerged motor pump whose pump and motor are immersed in a fluid, including: a pump impeller; a rotor coaxially mounted with said pump impeller for rotation together with said impeller; a rotor shaft rotatably supporting said rotor; a thrust bearing which supports said rotor shaft and receives a thrust load; and a pump housing including an end cover facing one end of said rotor shaft, said end cover having an interior surface in contact with the fluid and an exterior surface;
   a device for monitoring abrasion loss of the thrust bearing, said device comprising:
   a non-contact distance detector, mounted on said exterior surface of said end cover, separated from the fluid by said end cover, for generating a signal L representative of the the distance between said one end of said rotor shaft and said interior surface of said end cover; and
   calculator means for calculating the actual distance between said one end of said rotor shaft and said interior surface of said end cover in accordance with the signal L and sound velocity through the fluid.

2. A device for monitoring abrasion loss of a thrust bearing in a submerged motor pump according to claim 1, wherein the said interior surface of said end cover in contact with said fluid includes a member having a concave spherical surface to which said distance detector is affixed, said member separating said distance detector from the fluid.

3. A device for monitoring abrasion loss of a thrust bearing in a submerged motor pump according to claim 2, wherein said one end of said rotor shaft is defined by a cap nut.

4. A device for monitoring abrasion loss of a thrust bearing in a submerged motor pump according to claim 1, wherein said one end of said rotor shaft is defined by a cap nut.

5. A device for monitoring abrasion loss of a thrust bearing in a submerged motor pump according to claim 1, wherein said rotor shaft is vertically oriented and said one end is the lower end of said shaft.

6. A device for monitoring abrasion loss of a thrust bearing in a submerged motor pump according to claim 1, wherein said non-contact distance detector is an ultrasonic sensor which projects ultrasonic waves toward said one end of said rotor shaft and detects the echo of said ultrasonic waves reflected by said one end of said rotor shaft.

7. A device for monitoring abrasion loss of a thrust bearing in a submerged motor pump according to claim 6, wherein the said interior surface of said end cover in contact with said fluid includes a member having a concave spherical surface to which said distance detector is affixed, said member separating said distance detector from the fluid.

8. A device for monitoring abrasion loss of a thrust bearing in a submerged motor pump according to claim 7, wherein said one end of said rotor shaft is defined by a cap nut.

9. A device for monitoring abrasion loss of a thrust bearing in a submerged motor pump according to claim 7, wherein the rotor shaft, the apex of said concave spherical surface and said ultrasonic sensor are axially aligned.

10. A device for monitoring abrasion loss of a thrust bearing in a submerged motor pump according to claim 6, wherein said one end of said rotor shaft is defined by a cap nut.

11. A device for monitoring abrasion loss of a thrust bearing in a submerged motor pump according to claim 6, further comprising:
- a temperature sensor for detecting the temperature of the fluid between said one end of said rotor shaft and said interior surface of said end cover in contact with said fluid;
- a pressure sensor for detecting the pressure of the fluid between said one end of said rotor shaft and said interior surface of said end cover in contact with said fluid; and
- wherein said calculator means calculates said sound velocity through the fluid in accordance with temperature detected by said temperature sensor and pressure detected by said pressure sensor.

12. A device for monitoring abrasion loss of a thrust bearing in a submerged motor pump according to claim 11, wherein said calculator means calculates said actual distance in accordance with said calculated sound velocity and with a predetermined value for sound velocity through the fluid.

13. A device for monitoring abrasion loss of a thrust bearing in a submerged motor pump according to claim 12, wherein said rotor shaft is vertically oriented and said one end is the lower end of said shaft.

14. A device for monitoring abrasion loss of a thrust bearing in a submerged motor pump according to claim 6, wherein said rotor shaft is vertically oriented and said one end is the lower end of said shaft.

15. A device for monitoring abrasion loss of a thrust bearing in a submerged motor pump according to claim 6, wherein said ultrasonic sensor is mounted to project said ultrasonic waves coaxially with the rotor shaft.

* * * * *